United States Patent [19]

Hayes

[11] Patent Number: 4,492,220

[45] Date of Patent: Jan. 8, 1985

[54] VAGINAL SPECULUM PROTECTOR

[76] Inventor: Allen L. Hayes, 7362 Creekview, West Bloomfield, Mich. 48033

[21] Appl. No.: 441,703

[22] Filed: Nov. 15, 1982

[51] Int. Cl.³ .............................................. A61B 1/32
[52] U.S. Cl. .................................. 128/17; 128/132 R
[58] Field of Search ............................. 128/3, 17–19, 128/736, 132 R, 132 D, DIG. 24, 361

[56] References Cited

U.S. PATENT DOCUMENTS

| 3,215,265 | 11/1965 | Welin-Berger | 128/736 |
| 3,789,835 | 2/1974 | Whitman | 128/18 |
| 3,794,091 | 2/1974 | Ersek et al. | 128/132 R |
| 3,841,317 | 10/1974 | Awais | 128/9 |
| 3,878,836 | 4/1975 | Twentier | 128/17 |
| 3,934,582 | 1/1976 | Gorrie | 128/132 D |
| 4,197,944 | 4/1980 | Catlin | 128/736 |

FOREIGN PATENT DOCUMENTS 506409 5/1976 U.S.S.R. ................................. 128/3

Primary Examiner—Edward M. Coven
Assistant Examiner—Max F. Hindenburg
Attorney, Agent, or Firm—Krass & Young

[57] ABSTRACT

Disposable covers for the blades of a vaginal speculum are provided to prevent cross contamination of patients examined by the same instrument.

3 Claims, 3 Drawing Figures

VAGINAL SPECULUM PROTECTOR

DESCRIPTION

1. Technical Field

This invention relates to surgical instruments and, more particularly, to techniques for preventing cross contamination of patients examined by vaginal speculums.

2. Background Art

A vaginal speculum is an important medical instrument which serves as an expedient means for providing examination and treatment of the vagina and related areas. Examples of this relatively old instrument are found in U.S. Pat. Nos. 662,830 and 2,672,859.

A vaginal speculum comprises, briefly, a composite frame assembly having a pair of protruding blades which are inserted into the vagina and thereafter separated or opened to provide a channel for visual examination and treatment. Medical practitioners require a vaginal speculum which lends itself to manual dexterity. The design of conventional vaginal speculums enables the blades to be sufficiently movable to provide not only parallel but angularly displaced adjustment of the blades over a wide range of separation.

The most commonly used vaginal speculums are made of metal such as stainless steel and are designed to have long, useful lives. However, after each use the instrument must be cleaned and sterilized as a medical necessity to prevent transfer of harmful bacteria or other contamination from one patient to another. Such cleaning practices are time consuming as well as undesirable and menial tasks. At the same time these practices tend to limit the number of vaginal examinations which may be accomplished in a given time period unless a large number of these instruments are available. The number of vaginal examinations being performed has drastically increased in all areas of medical diagnosis and treatment. As a consequence, significant quantities of these relatively expensive instruments must be procurred thereby requiring a sizable investment even for the single practitioner.

Even if many instruments are available to the practitioner it is still difficult to insure absolute sterility using conventional methods of cleaning the vaginal speculum. The medical literature has reported several strains of bacterial spores which are particularly adapted for prolonged survival under adverse conditions. These strains are relatively resistant to killing by heat, as well as by drying, freezing, toxic chemicals and radiation. In fact, some of the more heat-resistant spores have been known to survive boiling for many hours. See, e.g., Davis et al, *Microbiology*, 3rd Edition, pages 102, 108; Freeman, *Textbook of Microbiology*, pages 122-131, and 819; and Joklik et al, *Zinsser Microbiology*, 17th Edition, pages 281-282, 292-294, 1341-1440. Hence, the possibility of cross contamination remains a very real possibility.

In an effort to prevent this cross contamination problem the art has almost exclusively directed its efforts towards providing disposable speculums which may be thrown away after the examination of one patient. Representative examples of disposable vaginal speculums disclosed in the patent literature are found in U.S. Pat. Nos. 3,815,585; 3,890,961; and 4,263,898. In general, these disposable instruments are made of plastic which by their nature are more resilient than the conventional permanent metallic speculums. Unfortunately, many of the disposable speculums are comparatively difficult to manipulate, do not provide a wide range of adjustment, or are much more expensive to use in the long run when compared to the permanent type of vaginal speculum.

OBJECT AND SUMMARY OF THE INVENTION

It is the primary object of this invention to provide a technique for using conventional, permanent type vaginal speculums and obtaining all of their recognized advantages while at the same time minimizing the possibility of cross contamination in an economical and less burdensome manner.

Pursuant to the present invention, a pair of disposable covers, one for each blade of the vaginal speculum, is provided. Each cover is adapted to surround and closely conform to substantially the entire length of both sides of the blades of the speculum. The covers are made of a suitable material that prevents bi-directional transfer of harmful bacteria or other organisms from the blade to the patient or vice versa. In the preferred embodiment, the covers are made of smooth plastic sheets adapted to slip over the distal end of the blades. The smooth surface of the plastic facilitates slipping the cover onto the speculum blade and insertion of the instrument into the patient. In the disclosed embodiment, the covers are formed of two oblong sheets of polyethylene having their forward and side edges fused together. A tab on a rear end of one of the sheets may be provided to aid in pulling the cover onto the blade.

According to the method of this invention a disposable cover is slipped onto each of the blades prior to examining the patient. After the examination the covers are removed and disposed. Then new covers are slipped onto the speculum blades prior to examining the next patient.

Among the advantages of the present invention is that the same permanent type vaginal speculum may be used for examining several patients while minimizing the chances of cross contamination. None of the manipulative features are impaired by use of the bacteria impervious covers. As a result, there are few disadvantages of using the concept of this invention and a host of advantages that can be achieved in a simple, low cost manner.

BRIEF DESCRIPTION OF THE DRAWINGS

These and other objects and advantages of the present invention will become apparent to one skilled in the art upon reading the following specification and by reference to the drawings in which.

DESCRIPTION OF THE PREFERRED EMBODIMENT

Figure 1:
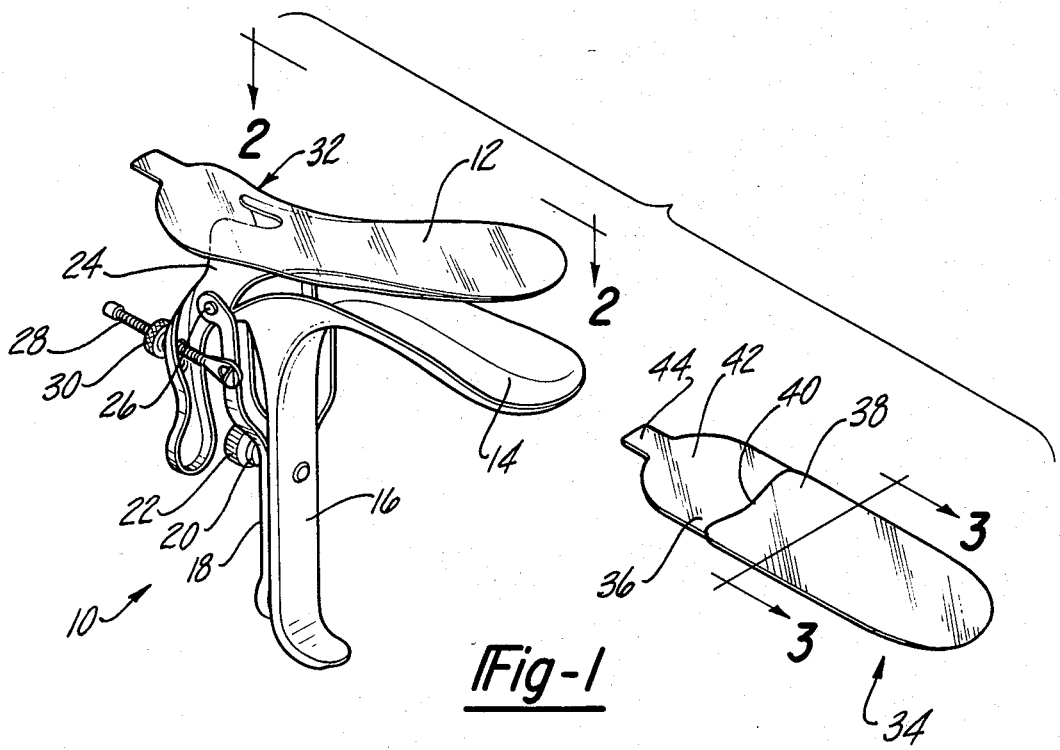
FIG. 1 is an exploded perspective view showing one cover of the preferred embodiment on the top blade of a vaginal speculum and the cover for the lower blade displaced therefrom.

Referring now to the drawings, a conventional vaginal speculum made of stainless steel or the like and adapted for a permanent use is designated by the reference numeral 10. Speculum 10 includes a pair of dilatory blades 12 and 14 which are pivotally and slidably coupled together for movement toward and away from each other. A handle 16 is formed integrally with blade 14. A blade positioning slide 18 is mounted on the handle 16 by a threaded bolt 20 which extends through a slot in the slide. A knurled nut 22 is threaded onto bolt 20 and serves to lock the handle 16 and slide 18 together. When the nut 22 is loosened, the slide 18 can be translated along the handle 16 between the extreme positions defined by the ends of the slot.

A depending adjustment arm 24 is formed integrally with the rearward portion of the top blade 12. A rivet 26 extends through aligned apertures in the slide 18 and arm 24 to pivotally mount the blade 12. An adjusting screw 28 connects one end region of arm 24 with the slide 18. A knurled nut 30 is threaded onto adjusting screw 28 and serves to retain the blade 12 at a selected provided position relative to the lower blade 14.

The construction of speculum 10 as thus far described is old in the surgical art. Speculum 10 is intended for repeated use and is commonly made of stainless steel or other metals which will withstand repeated sterilization. Hereinafter, these conventional speculums shall be referred to as permanent speculums. In use, permanent speculums are manipulated so as to close the blades 12, 14 for insertion into the patient and then adjusted to space the blades to provide a viewing area for the physician.

Figure 2:
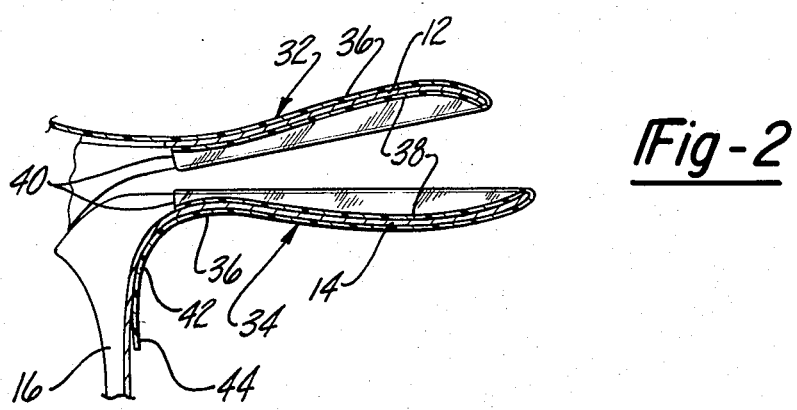
FIG. 2 is a fragmentary side cross-sectional view along the lines 2—2 of FIG. 1 showing both covers in place.
Figure 3:
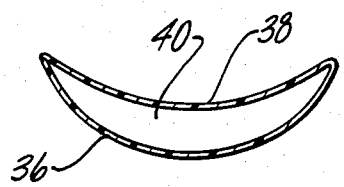
FIG. 3 is a cross-sectional view along the lines 3—3 of FIG. 1.

Pursuant to the present invention a pair of of sterile covers 32, 34 are provided for covering those portions of blades 12, 14, respectively, that are designed to come into contact with the patient during examination. Each of the covers 32, 34 are identical and, thus, a description of the construction for one of them will suffice. The covers take the form, in the preferred embodiment, of thin walled bags formed by generally coextensive sheets 36, 38 of material which are joined together at their forward and side edges. The overlapping portions of sheets 36 and 38 extend substantially the entire length of its respective blade as shown most clearly in FIG. 2. As shown therein, the covers are dimensioned so that they closely conform to both the upper and lower portions of their respective blades.

The non-joined rearward edge 40 of sheets 36, 38 defines an elongated opening so that the covers may be slipped onto the blades. In the preferred embodiment, the nonoverlapped portion 42 of sheet 34 is of sufficient length so that it may serve to protect the forward upper portion of the speculum handle 16 from coming into contact with the outer tissues of the patient. The rear extremity of the sheet 36 may include a tab portion 44 which may be grasped by the user to aid in slipping the cover onto the blade without touching the cover portions that may come into contact with the patient.

In the particular example disclosed herein, covers 32, 34 are made of sheets of smooth plastic such as polyethylene whose forward and side edges have been fused together under heat and pressure.

In use, the covers 32 and 34 are grasped by their respective tab portions 44 and slipped onto the distal end of blades 12 and 14, respectively. Note that the smooth surface provided by the covers reduces friction and enables the covers to be positioned on the blades easily. Note also that while the covers 32 and 34 are identical, the lower cover 34 is rotated 180° about its longitudinal axis for use with the lower blade 14. In such manner, not only is the blade 14 covered but the nonoverlapping rearward portion 42 of the cover is brought into position in front of the upper portions of the handle 16. The covered speculum blades are then inserted into the patient and the speculum 10 adjusted to dilate the vagina by adjusting the position of the blades using the same techniques as the physician normally uses with the conventional speculum 10. Because the covers 34, 36 closely conform to the blades, the physician's view is not obstructed. Since separate covers are provided for each of the blades the side walls of the vaginal area are not obstructed from view and may be accessed for treatment. The smooth surfaces of the covers also facilitate easy insertion of the instrument and minimize abrasion. Since lubricants for the blades cannot generally be used, the covers thus provide an added benefit in that they minimize the discomfort often experienced by the patient when conventional uncovered speculums are used. The covers also give the feeling of warmth not normally experienced with bare metal coming into contact with the patient.

One of the most important advantages of the present invention is that the covers prevent the transfer of harmful bacteria, viruses or other organisms from the blades to the patient and vice versa. The covers isolate not only the outer surfaces of the blades from the patient but also the substantial entirety of the inner portions of the blades as well. Consequently, the chances of cross contamination of patients being examined by the same instrument is substantially minimized.

After the examination is completed, the blades are adjusted so that they become closely spaced and the instrument is removed from the patient. Note that the design of the covers still permit the practitioner to obtain access to all of the adjustment devices of the conventional speculum. After the instrument has been removed, the covers are grasped by the tab portions (which generally do not come into contact with the patient) and the covers are slipped off of the blades and thrown away. New covers are then slipped over the blades of the speculum for examining the next patient.

It is believed that the covers of the present invention will eliminate the need for scrubbing and autoclave sterilization of the instrument between uses. A simple wash in cold sterilization solution and drying in air may be all that is necessary. The use of the covers also has the added benefit of minimizing the possibility of infecting the nurses or physicians that clean the instrument. Finally, it should be understood that while this invention has been described in connection with a particular example thereof, other modifications and advantages of the invention will become apparent to one skilled in the art after a study of the specification, drawings and following claims.

I claim:

1. A pair of identical disposable covers for use with a vaginal speculum of the type including a lower elongated blade, an upper elongated blade pivotally mounted at its rearward end to the rearward end of the lower blade, and a handle formed integrally with the rearward end of the lower blade and extending downwardly therefrom:

A. each cover comprising first and second elongated sheets of a smooth, compliant, plastic material,
   1. said first elongated sheet having a size and shape conforming to a speculum blade surface,
   2. said second elongated sheet having a forward portion overlying and conforming to said first sheet and a rearward portion extending rearwardly from the rearwardly edge of the first sheet;

B. said sheets being suitably joined together along their forward edges and along their confronting side edges to form a pocket opening at the rearward edge of said first sheet;
C. said covers being configured and dimensioned to slip smoothly over the free end of each blade to a fitted position snuggly conforming to the respective blade;
D. One of said covers, when positioned second sheet up and fitted over the upper speculum blade, having its first sheet covering substantially all of the lower surface of that blade, the forward portion of its second sheet covering the upper surface of that blade, and the rearward portion of its second sheet extending rearwardly of the rearward end of that blade to facilitate application and removal of the cover;
E. the other of said covers, when positioned first sheet up and fitted over the lower speculum blade, having its first sheet covering substantially all of the upper surface of that blade, the forward portion of its second sheet covering the lower surface of that blade, and the rearward portion of its second sheet extending downwardly in front of and in juxtaposition to the handle of the speculum to preclude contact between the patient and the handle.

2. A pair of covers according to claim 1 wherein said second sheet of each cover includes a tab portion on the rearward end of the rearward portion thereof which may be grasped by the user to pull the cover onto the respective speculum blade without touching the portions of the cover that surround the blade and come into contact with the patient.

3. A pair of covers according to claim 2 wherein each cover comprises polyethylene sheets fused together along their forward and side edges.

* * * * *